US009271829B2

(12) United States Patent
Bühren et al.

(10) Patent No.: US 9,271,829 B2
(45) Date of Patent: Mar. 1, 2016

(54) METHOD FOR THE PRE-OPERATIVE SELECTION OF AN INTRAOCULAR LENS TO BE IMPLANTED IN AN EYE

(75) Inventors: Tobias Bühren, Magdala (DE); Michael Trost, Stadtroda (DE)

(73) Assignee: Carl Zeiss Meditec AG, Jena (DE)

( * ) Notice: Subject to any disclaimer, the term of this patent is extended or adjusted under 35 U.S.C. 154(b) by 153 days.

(21) Appl. No.: 14/122,370

(22) PCT Filed: May 30, 2012

(86) PCT No.: PCT/EP2012/060176
§ 371 (c)(1),
(2), (4) Date: Nov. 26, 2013

(87) PCT Pub. No.: WO2012/163980
PCT Pub. Date: Dec. 6, 2012

(65) Prior Publication Data
US 2014/0192317 A1     Jul. 10, 2014

(30) Foreign Application Priority Data
May 31, 2011   (DE) .......................... 10 2011 103 223

(51) Int. Cl.
A61B 3/14       (2006.01)
A61F 2/16       (2006.01)
A61B 3/10       (2006.01)
A61B 3/00       (2006.01)

(52) U.S. Cl.
CPC ................. *A61F 2/16* (2013.01); *A61B 3/0025* (2013.01); *A61B 3/10* (2013.01); *A61F 2/1613* (2013.01)

(58) Field of Classification Search
CPC ..................................... A61B 3/13; A61B 3/16
USPC .......................... 351/206, 246, 221; 623/6.11
See application file for complete search history.

(56) References Cited

U.S. PATENT DOCUMENTS

| 5,968,095 | A | 10/1999 | Norrby |
| 8,216,305 | B2 * | 7/2012 | Salvati et al. ................ 623/6.11 |
| 2004/0263786 | A1 | 12/2004 | Williams et al. |
| 2007/0260157 | A1 | 11/2007 | Norrby |
| 2007/0268453 | A1 | 11/2007 | Hong et al. |
| 2009/0251664 | A1 | 10/2009 | Norrby et al. |
| 2010/0134760 | A1 | 6/2010 | Salvati et al. |

OTHER PUBLICATIONS

Preussner, P.-R. et al; "Intraocular lens calculation accuracy limits in normal eyes," J Cataract Refract Surg—vol. 34, May 2008; 802-808.
(Continued)

*Primary Examiner* — Hung Dang
(74) *Attorney, Agent, or Firm* — Patterson Thuente Pedersen, P.A.

(57) ABSTRACT

A method for the preoperative selection of an intraocular lens to optimise the results of refractive surgery on the eye. On the basis of an eye model comprising the individual biometric parameters of the eye, potentially suitable IOLs are selected on the basis of their optical parameters such as optical power, asphericity and toricity, and the residual refraction of potentially suitable IOLs is calculated using ray tracing. Various metrics, preferably retinal image metrics, are used to calculate the residual refraction and in order to improve the selection, at least one additional parameter is taken into consideration for the calculation, said calculation taking the postoperative effects of the selected IOL and/or of the surgical technique used into account.

30 Claims, 4 Drawing Sheets

(56) References Cited

OTHER PUBLICATIONS

Preussner, P.-R. et al; "Ray tracing for intraocular lens calculation," J Cataract Refract Surg—vol. 28, Aug. 2002; 1-10.
Einighammer, J. et al; "Customized aspheric intraocular lenses calculated with real ray tracing," J Cataract Refract Surg—vol. 35, Nov. 2009, 1984-1994.
Thibos, L.N., et al; "Accuracy and precision of objective refraction from wavefront aberrations," Journal of Vision (2004) 4, 329-351.
Fan Yi, et al; "Estimation of the depth of focus from wavefront measurements," Journal of Vision (2010) 10(4):3, 1-9.
Notification of Transmittal of Translation of the International Preliminary Report on Patentability (Chapter I or Chapter II) PCT/IB/338, PCT International Preliminary Report on Patentability Form PCT/IB/373, PCT Written Opinion of the International Searching Authority PCT/ISA/237 for PCT/EP2012/060176 (7 total pages), Dec. 19, 2013.

* cited by examiner

METHOD FOR THE PRE-OPERATIVE SELECTION OF AN INTRAOCULAR LENS TO BE IMPLANTED IN AN EYE

RELATED APPLICATIONS

The present application is a National Phase entry of PCT Application No. PCT/EP2012/060176, filed May 30, 2012, which claims priority from DE Application No. 10 2011 103 223.5, filed May 31, 2011, which applications are hereby incorporated by reference herein in their entirety.

FIELD OF THE INVENTION

The present invention relates to a method for the pre-operative selection of an intraocular lens to be implanted in an eye in order to optimize the results of refractive interventions in the eye.

BACKGROUND

According to the known prior art, IOLs are selected or adapted based on measured and/or estimated variables, only individual parameters in the form of individual measured values or as a mean for a defined patient group being taken into account.

The optimal intraocular lens (IOL) is selected or adapted exclusively according to its features, such as for instance type, refractive power, asphericity, and multifocality. No consideration is given to potential interrelationships with specific contributing factors to the treatment, such as patient features, diagnostics, surgical procedures, or the like, or to using statistical distribution for the parameters.

Cataract surgeons are required to select suitable intraocular lenses (IOL) for a patient. The surgeon must account for many factors. Firstly, the suitable calculation method for the IOL optical power must be selected. For this, as a rule different more or less suitable formulas must be used for the calculation for unusually long, normal, or unusually short eyes. In the simplest cases, the input parameters for these calculations are based on the keratometry and axial length of the eye. Due to their simplified model assumptions, the formulas generally also include an empirically determined correction factor, such as for instance the so-called A constant.

The currently most widely used calculation methods are so-called IOL formulas, e.g. Holladay, Hoffer, Binkhorst, Colenbrander, Shammas, and SRK IOL formulas. According to these, the refraction D (starting/evaluation parameter) of the patient after IOL insertion is calculated with:

$$D = D_{IOL} - f(K, AL, ACD, A) \quad (1)$$

where f( ) is a classically known IOL formula and
$D_{IOL}$ is the refractive power of the IOL,
K is the measured keratometry value,
AL is the measured axial length of the eye,
ACD is the measured anterior chamber depth, and
A is an IOL type-dependent constant input variable.

For selecting the IOL, the doctor specifies a target refraction ($D = D_{TARGET}$). For optimization, the doctor calculates the refraction in accordance with (1) for different IOLs by varying $D_{IOL}$ and A. In many cases the doctor uses IOLs of the same type so that there is no variation in A and the optimization amounts to a formula calculation according to $D_{IOL} = D_{TARGET} + f(K, AL, ACD, A)$. Thus, if the target is emmetropia, the classic formula calculation for the IOL that results is $D_{IOL} = f(K, AL, ACD, A)$.

The constant A in the formulas is determined empirically using a patient ensemble in order to adapt the formula values to the actually resulting optimal refraction values. However, this adaptation only ensures that the mean of the refraction values for the test ensemble agrees with the formula.

The doctor typically accounts for statistical errors in the biometry formula in that he knows from experience that his actually attained refraction values for his patients will have a certain fluctuation around the target refraction. If he wants to minimize its effect, he provides a correction to the target refraction. For instance, if the doctor typically has deviations of +/−0.25 D for target refraction in patients with myopic eyes, then he will target refraction of −0.25 D in order to have a high probability of preventing the eye of the patient from being intolerably hyperopic. This method represents a good strategy for the average in the patient ensemble.

However, the typical fluctuation around the target refraction or the allowance could be reduced if, instead of a mean value for a patient ensemble, individual input parameters for the individual patient were to be used as the initial variables.

Currently various approaches are used according to the prior art in order to minimize systematic errors.

Thus, a number of doctors use a different. A constant for each ethnic group among their patients. This permits a reduction in the systematic errors and also permits a reduction in statistical errors if the statistical variance in each group is lower.

Depending on defined starting conditions such as for instance patients having long axial eye lengths or that have had previous refractive corneal surgery, other doctors use different biometric formulas that are better adapted to the conditions in a specific case or that require measurement of additional parameters, such as the anterior chamber depth or lens thickness. In this case, as well, in particular the systematic errors are reduced, but statistical errors may increase due in part to the additional measured parameters.

Thus for instance U.S. Pat. No. 5,968,095A describes a method for pre-operative selection of an intraocular lens in which it is to be assured that the eye has a desired post-operative refractive power. This is to be attained in that the location of the lens haptic plane, the corneal refractive power of the eye, and the axial length of the eye are determined and the desired post-operative refractive power is selected. For an IOL to be implanted, the refractive power and geometry of which are known, an offset between the lens haptic plane and the anterior vertex of the lens is prespecified as if it were in its implanted condition. Then a calculation is made to check whether the focus of the selected IOL, with the aforesaid specifications and the refraction indices of the ocular fluids, will fall post-operatively onto the retina of the eye. If this is not the case, the calculation is performed over again for a different IOL having a different refractive power and/or geometry. For the implantation, an available IOL of nearest refractive power for which focusing on the retina has been calculated is selected for the implantation.

An alternative method, albeit a method that is not widely used, is ray tracing. As the term indicates, ray tracing shall be construed as a method for tracing/following rays. As is known, we only perceive objects in our environment because they are irradiated by a light source and they reflect these rays of light, some of which ultimately reach our eyes. The ray tracing method simulates this elementary natural phenomenon. If the optical system, i.e., the individual human eye with all of its optical elements, is known, a "real" image occurring on the retina may be calculated by means of ray tracing. The method is thus based on a detailed eye model using the corneal topography of the eye. In this method, no general correction factors (A constants) are used, but certain assumptions regarding the effective (post-operative) lens position (ELP) must be made. This method is suitable for eyes having widely varying biometric parameters, such as for instance long eyes, normal eyes, short eyes, post-LASIK eyes, etc.

The IOL optical power and the residual refraction are then calculated using ray tracing. Various selection criteria and metrics for the calculation may be used in order to attain a good correlation to subjective visual acuity, i.e. a result comparable to what the patient experiences. Although retinal image metrics have proved to be particularly suitable, the following other selection criteria are also possible:

Evaluation of the image on the retina with respect to moment, entropy, compactness, shape, and intensity distribution by means of point spread function (PSF), line spread function (LSF), and root mean square;

Evaluation of resolution using optical transfer function (OTF), such as modulation transfer function (MTF) or phase transfer function (PTF);

Evaluation of contrast using the contrast sensitivity function (CSF);

Evaluation of optical aberrations, such as chromatic aberration, ray aberration, wavefront aberration, depth of field, and binocular deviation of the image scale;

Evaluation of the classic refraction parameters: diopter and astigmatism.

This list merely provide examples, because in principle other optical evaluation parameters known to one skilled in the art may also be used. In addition, in principle any evaluation parameters or criteria with which deviations from the ideal wavefront may be assessed and quantified may be used.

U.S. Pat. No. 7,357,509 B2 describes some metrics that are particularly suitable for predicting the subjective impacts of wavefront aberrations of an eye. The metrics used may be based on the effective values or the increase in wavefront errors, the area of the critical pupil, a curvature parameter, the point spread function, the optical transfer function, or the like.

While P.-R. Preussner et al [1] compare the use of ray tracing methods and IOL formulas, publication [2] goes into more detail regarding a calculation model that is based on a method of ray tracing. In this case, based on the individual measured values and estimated variables such as especially the position of the IOL in the eye, an eye model with as a rule a plurality of optically active surfaces is developed and is calculated for one or a plurality of rays using methods from the optical design. The image quality on the retina/fovea is calculated as the evaluation value. With appropriately precise determination of the input variables this makes it possible to avoid systematic errors to a large extent. Statistical errors that result for example from lack of reproducibility of measurements or from fluctuations in the wound healing process are not taken into account here, either.

J. Einighammer et al describe another method for calculating the exact geometry of customized IOLs for pseudophakic eyes that is based on ray tracing in [3]. An individual calculation model is designed using measurements. During the optimization process, which includes the geometry of the customized IOL, so-called real ray tracing is used to try to obtain the minimum of wavefront errors.

In [4], L. N. Thibos et al investigate the extent to which the use of different metrics, such as for instance pupil plane and image plane metrics, impact the accuracy and precision of predicting the results of wavefront aberrations. It was found that there are certainly differences in the precision of predictions, but that the accuracy of all methods may be improved by correcting systematic bias.

In addition to the IOL optical power, certain parameters, such as asphericity and toricity or the cornea, provide indications for certain IOLs. In the case of so-called premium IOLs, after consulting with the patient, the surgeon may decide in favor of IOLs that satisfy specific visual tasks, such as e.g. multi-focal lenses. Such IOLs should make it possible for the patient to perform visual tasks in the near range and far range without additional vision aids. How the IOLs used in the individual eyes actually satisfy the requirements imposed on them is a function of a number of factors, such as for instance the optics of the cornea, the implantation technique, the optical and mechanical design of the IOL, the pathologies of the eyes, etc.

LITERATURE

[1] Preussner, P.-R. et al; "Intraocular lens calculation accuracy limits in normal eyes," J CATARACT REFRACT SURG—VOL 34, May 2008;

[2] Preussner, P.-R. et al; "Ray tracing for intraocular lens calculation," J CATARACT REFRACT SURG—VOL 28, AUGUST 2002;

[3] Einighammer, J. et al; "Customized aspheric intraocular lenses calculated with real ray tracing," J CATARACT REFRACT SURG—VOL 35, NOVEMBER 2009;

[4] Thibos, L. N., et al; "Accuracy and precision of objective refraction from wavefront aberrations," Journal of Vision (2004) 4, 329-351;

[5] Fan Yi, et al; "Estimation of the depth of focus from wavefront measurements," Journal of Vision (2010) 10(4): 3, 1-9.

SUMMARY OF THE INVENTION

The invention includes a method for pre-operative selection of an intraocular lens to be implanted in an eye, in which method the decision for the selection of an IOL is not so very dependent on the experience of the doctor. On the contrary, according to embodiments of the invention it should be possible for the doctor to compare potentially suitable IOLs to one another and to take into account particular requirements, criteria, and parameters during the selection process. This should simplify the selection process and improve the result of the refractive intervention in the eye.

With the inventive method for the pre-operative selection of an IOL that is to be implanted in an eye, based on an eye model having the individual biometric parameters of the eye, in which method potentially suitable IOLs are selected using their optical parameters such as optical power, asphericity, and toricity, and the residual refraction is calculated by means of ray tracing for the potentially suitable IOLs, attained in that for calculating the IOL optical power and the residual refraction, various metrics are used, for example retinal image metrics, and in that for improving the selection at least one additional parameter that takes into account the post-operative effects of the selected IOL and/or the surgical technique used is included in the calculation.

While eye operations that change the total refractive power of the eye, and thus replace or at least sharply reduce the severity of conventional optical corrections such as eyeglasses and contact lenses, are included in the term refractive surgery, the suggested solution relates to a method for pre-operative selection of an IOL to be implanted in an eye during a refractive intervention.

During such an intervention, a probe is inserted through a small incision into the eye. Using ultrasound, it comminutes the lens and removes the constituent parts. The removed lens is then replaced by an IOL made of plastic that is inserted through the same incision.

Although the suggested method only describes the pre-operative selection of an IOL for a refractive lens replacement, in principle it is also suitable for the selection of artificial intraocular lenses that are also inserted into the anterior chamber of the eye (between cornea and iris) or the posterior chamber of the eye (between iris and lens).

BRIEF DESCRIPTION OF THE DRAWINGS

The invention shall be described in greater detail in the following using example embodiments.

DETAILED DESCRIPTION

In the inventive method for pre-operative selection of an intraocular lens (IOL) to be implanted into an eye, based on an eye model having the individual biometric parameters of the eye, potentially suitable IOLs are selected using their optical parameters, such as optical power, asphericity, and toricity, and the residual refraction for the potentially suitable IOLs is calculated by means of ray tracing. Various metrics, for example retinal image metrics, are used for calculating the residual refraction and an additional parameter that takes into account the post-operative effects of the selected IOL and/or the surgical technique is included in the calculation.

In addition to prior, conventionally available information, such as the optical power, asphericity, and toricity of the IOL, new quantitative parameters are available to the cataract surgeon and enable a quantitative selection of the IOL for the individual case.

In this context, the influence of the design of the IOL on pseudoaccommodation, i.e. the useable depth of field, and the lens tolerance for the IOL are of great interest. Incorrect positioning may for instance result in unexpected, post-operative changes during the healing process.

In addition to the usable depth of field and incorrect post-operative positioning, the following quantitative criteria are also of interest in the selection process:
Preferred range of visual tasks;
Pre-operative diagnosable pathological indications; and,
Incision technique, including Limbal Relaxing Incision (LRI)

In a first embodiment of the inventive method, the post-operative achievable depth of field is included as an addition parameter during the selection of the IOL to be implanted in an eye.

A prerequisite for calculating the achievable depth of field for an IOL-eye combination is the creation of an eye model having the individual biometric parameters of the eye in question. In addition to the corneal topography (curvature of the anterior surface or anterior and posterior surfaces of the cornea) and the biometry (axis length and anterior chamber depth) of the eye, as well as the parameters of the IOL, an assumption relating to the effective lens position (ELP) is also required for this.

The residual refraction is then calculated by means of ray tracing, it being possible to use different selection criteria or metrics for the calculation. It is obvious to use retinal image metrics, which enable a good correlation with subjective visual acuity, i.e. a result that is comparable to the perception of the patient.

The post-operatively achievable depth of field is taken into account such that, with the metrics used, for example, retinal image metrics for the post-operatively achievable depth of field, a limit for a minimum visual acuity is established and from this the usable visual tasks range for the potentially suitable IOLs is determined and used as a selection criterion.

Figure 1A:
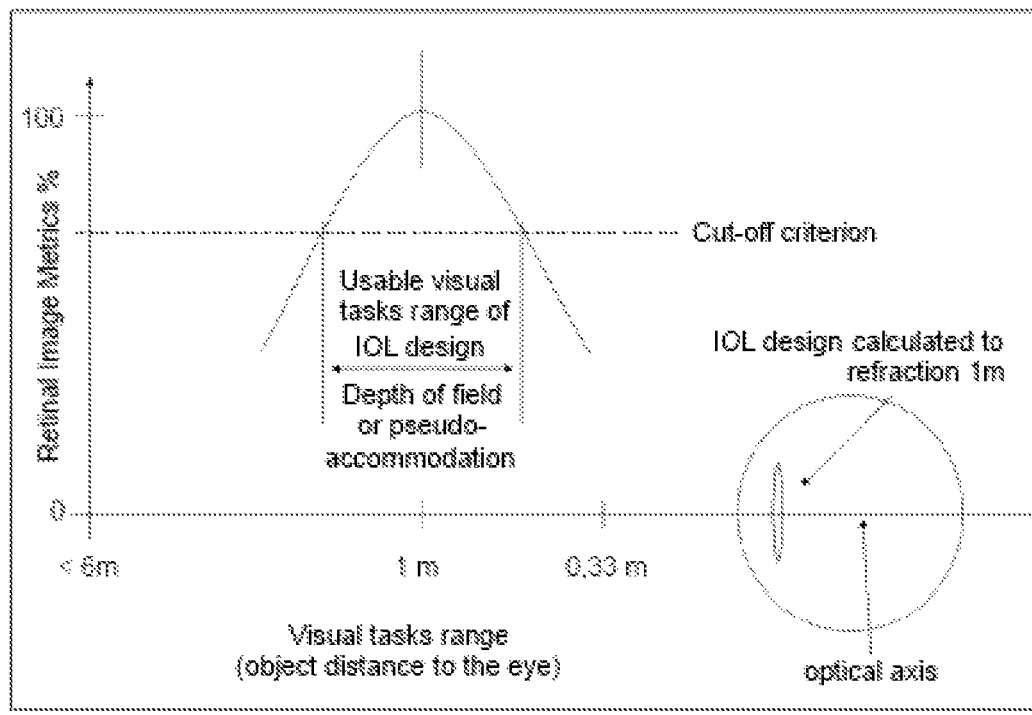
FIG. 1a: depicts the curve for visual acuity as a function of distance to the eye for an IOL with near refraction.
Figure 1B:
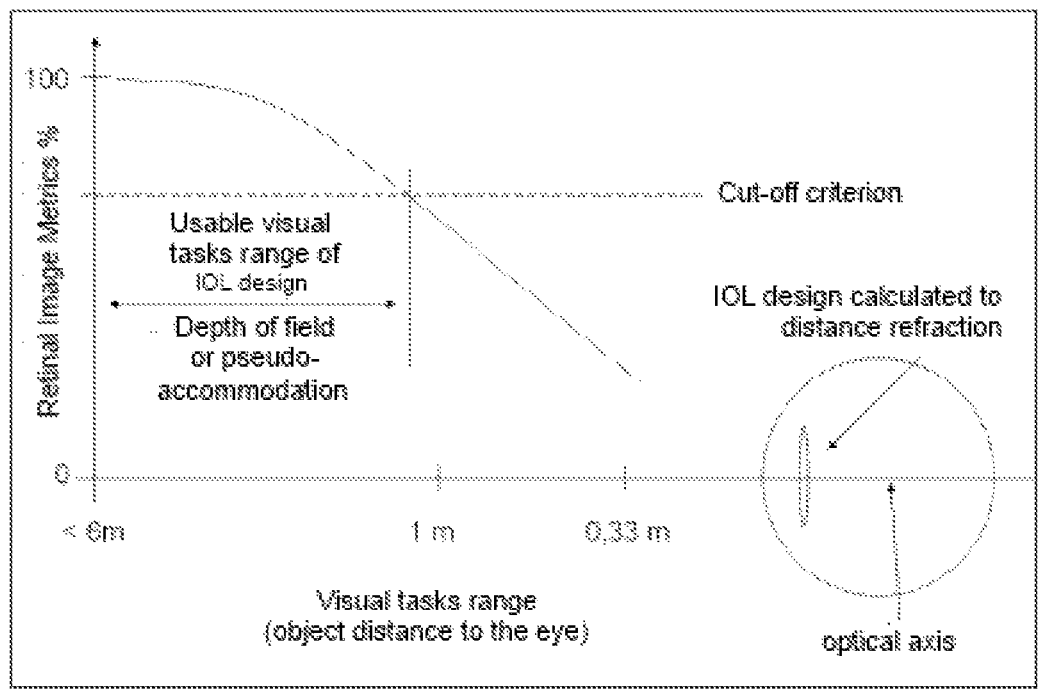
FIG. 1b: depicts the curve for visual acuity as a function of distance to the eye for an IOL with distance refraction.

To this end, FIG. 1a and FIG. 1b depict the curves for visual acuity as a function of distance to the eye for IOLs with different refraction tasks.

FIG. 1a depicts the curve for visual acuity as a function of the distance to the eye for an IOL having near refraction. Proceeding from the eye, corresponding to the specification (near refraction) the maximum simulated visual acuity (approx. 100%) is achieved with the IOL refractive power at a distance of about 1 m, based on retinal image metrics. Then a value of for instance 80% is established as the limit for a simulated minimum visual acuity and is drawn in as a straight line, the same retinal image metrics being used. The segment between the two points of intersection for simulated visual acuity curve and minimum visual acuity identify the post-operative achievable depth of field.

Proceeding from the specification for near refraction, it is now possible to select the IOL that for instance achieves the greatest post-operatively achievable depth of field around this near point (of 1 m). This simultaneously corresponds to the usable visual tasks range and is also called pseudoaccommodation, since the patient has the impression that his artificial eye lens can focus in this range. The value in diopters for the IOL is found from the required distance at which the overall system attains the maximum of the simulated visual acuity within the usable visual tasks range. The value may also vary within the usable field of view. The analysis may in particular serve as an objective decision-making aid during the selection of different designs of IOLs for an individual eye.

In contrast, FIG. 1b depicts the curve for visual acuity as a function of distance to the eye for an IOL having distance refraction. Proceeding from the eye, the maximum visual acuity (of 100%) is achieved with this IOL at a distance of >6 m. A limit for minimum visual acuity is then established and drawn into the curve, the same retinal image metrics being used. The segment between the two points of intersection between the curve for simulated visual acuity and minimum visual acuity identifies the usable visual tasks range.

Proceeding from the requirement for distance refraction, it is possible to select the IOL that for instance achieves the greatest post-operatively achievable depth of field around this distance point (of >6 m). This range simultaneously corresponds to the usable visual tasks range and is also called pseudoaccommodation.

Although this has proved advantageous, the limit for minimum visual acuity does not have to be 0.8, but rather may for instance even be 0.7 or 0.5 or even less.

In this context, in [5] Fan Yi et al describe how the achievable depth of field may be estimated directly from wavefront measurements using different retinal image quality metrics. Corresponding threshold values that in the present case were 50% and 80% were also assumed.

In a second example embodiment of the inventive method, the preferred visual tasks range is taken into account as an additional parameter.

In this embodiment, the visual tasks range preferred by the patient is taken into account such that, with the metrics used, for example retinal image metrics, potentially suitable IOLs are determined that correspond to the visual tasks range preferred by the patient and achieve a sufficiently high post-operative depth of field.

In contrast to the previously described embodiment of the method, in this case it is not a requirement that is specified in the form of a near refraction or distance refraction, but rather the visual tasks range preferred by the patient.

For the preferred visual tasks range, the curve for visual acuity is calculated a function of the distance to the eye for potentially suitable IOLs. The preferred visual tasks range is then defined in the form of two vertical lines in the curve, the same retinal image metrics being used.

Proceeding from the specification of near refraction, it is now possible to select the IOL that best covers the preferred visual tasks range. The value in diopters for the IOL results from the required distance at which the overall system achieves the maximum simulated visual acuity within the usable visual tasks range. The value may also vary within the usable visual range.

In addition to the preferred visual tasks range, the post-operatively achievable depth of field for the potentially suitable IOL may be controlled in a simple manner.

Figure 2:
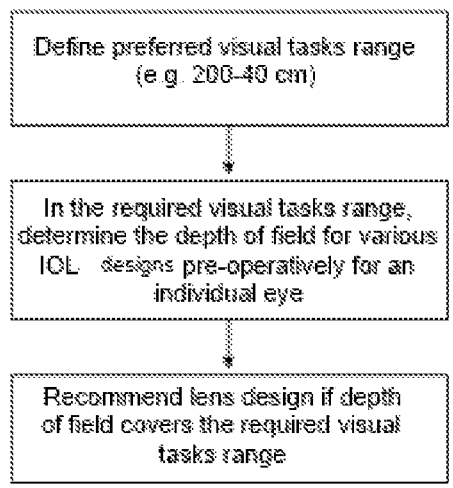
FIG. 2: is a flowchart for the quantitative selection of an IOL as a function of the preferred visual tasks range.

For this, FIG. 2 provides a flowchart of the quantitative selection of an IOL as a function of the preferred visual tasks range. Proceeding from the preferred visual tasks range, the curve for visual acuity is determined as a function of the distance to the eye for potentially suitable IOLs. The IOL recommended for transplantation is the IOL that best covers the preferred visual tasks range. In addition, for decision-making the post-operatively achievable depth of field for the potentially suitable IOL may be controlled.

It may particularly advantageous to take into account parameters specific to the patient or to his eye. To prevent a patient who is suffering from myopia from suffering from hypermetropia-after the implantation, an IOL is selected for implantation, for instance, the optical power of which is towards the lower end of the preferred visual tasks range.

In a third example embodiment of the method, the IOL tolerance with respect to incorrect post-operative positioning in the eye is taken into account as an additional parameter.

The lens tolerance with respect to incorrect post-operative positioning of the IOL is taken into account such that a characteristic number LT is quantified for a clinically likely incorrect positioning. The quantified characteristic number LT includes at least incorrect positioning perpendicular to the visual axis in the vertical and horizontal directions or along the visual axis or a tilt in the vertical and horizontal directions or a rotation about the visual axis. Incorrect positioning due to rotation about the visual axis plays a role only in the implantation of non-rotationally symmetrical lenses, e.g. toric lenses.

This means that incorrect positioning of the IOL may be present in only one direction, e.g. along the visual axis, or, due to rotation about the visual axis, even in several directions, e.g. due to tilting in the vertical and horizontal directions, or even in all of the aforesaid directions. The quantification of the characteristic number LT changes accordingly.

The deviation from the calculated target refraction of an individual IOL due to incorrect positioning of the IOL in the eye is a function of different parameters that are influenced both by the IOL and by the eye. Therefore it is important to know the parameters of the eye. The pre-operative evaluation of the quantified characteristic number LT for an individual IOL-eye combination may therefore be quantified as a characteristic number as follows using an individual eye model for clinically likely incorrect positioning:

$$LT = \sqrt{\frac{(Dez(\pm X))^2 + (Dez(\pm Y))^2 + (Dez(\pm Z))^2 + (Kip(\pm X))^2 + (Kip(\pm Y))^2 + (Rot(\pm Z))^2}{6}} \quad (2)$$

where LT defines the characteristic number for tolerance $Dez(\pm X)$ defines the spherical equivalent (Sph+Zyl/2) of the horizontal deviation from the target refraction $Dez(\pm Y)$ defines the spherical equivalent (Sph+Zyl/2) of the vertical deviation from the target refraction $Dez(\pm Z)$ defines the spherical deviation from the target refraction due to axial displacement $Kip(\pm X)$ defines the spherical equivalent (Sph+Zyl/2) of the deviation from the target refraction due to horizontal tilt $Kip(\pm Y)$ defines the spherical equivalent (Sph+Zyl/2) of the deviation from the target refraction due to vertical tilt $Rot(\pm Z)$ defines the resultant cylindrical deviation from the target refraction due to axial rotation wherein all values are calculated and/or provided in diopters, in units of retinal image metrics, or even in relative units.

Although Formula (2) is a very elegant and simple method for quantifying the characteristic number LT, it represents only one possible method.

First of all, it is possible to take into account a clinically likely incorrect positioning in that the characteristic number LT is determined for potentially suitable IOLs using a defined incorrect positioning, i.e. for decentration and/or tilt and/or rotation.

Secondly, it is also possible to take into account a clinically likely incorrect positioning in that the characteristic figure LT is not determined using a defined incorrect positioning, but rather that with a given characteristic number LT the degree of the "allowable" incorrect positioning is determined for potentially suitable IOLs.

The degree of decentration, tilt, and rotation is selected such that a clinically reasonable evaluation of the quantified characteristic number LT becomes possible. The clinically possible ranges for decentration (Dez), tilt (Kip), and rotation (Rot) may be defined as follows:

$Dez(X) = \pm 0.00$ mm to $\pm 10.00$ mm $Dez(Y) = \pm 0.00$ mm to $\pm 10.00$ mm $Dez(Z) = \pm 0.00$ mm to $\pm 10.00$ mm $Kip(X) = \pm 0.00°$ to $\pm 50°$ $Kip(Y) = \pm 0.00°$ to $\pm 50°$ $Rot(Z) = \pm 0.00°$ to $\pm 90°$

As mentioned in the foregoing, all of the characteristic numbers for determining LT may be calculated and/or provided in diopters, in units of retinal image metrics, or even in relative units.

In a fourth example embodiment of the method, for improving the selection an additional parameter that takes into account the pre-operative features of the eye, in particular pre-operative diagnosable pathological indications, is included in the calculation.

This has the advantage that the measured, pre-operatively diagnosable pathological indications may be taken into account as expected post-operative fluctuations in the target refraction.

Thus for example the values for decentration and/or tilt of the natural eye lens relative to the center of the pupil and/or limbus may be measured and expected post-operative values may be determined therefrom.

One indication of decentration and tilt of the natural eye lens may be weak zonular fibers. Since as a rule these also hold the IOL, the likelihood of decentration and/or tilt of the IOL is correspondingly high.

In order to allow for this, IOLs whose tolerances with respect to incorrect post-operative positioning are correspondingly high should be sought, i.e. the likelihood of their being incorrectly positioned is correspondingly low.

Figure 3:
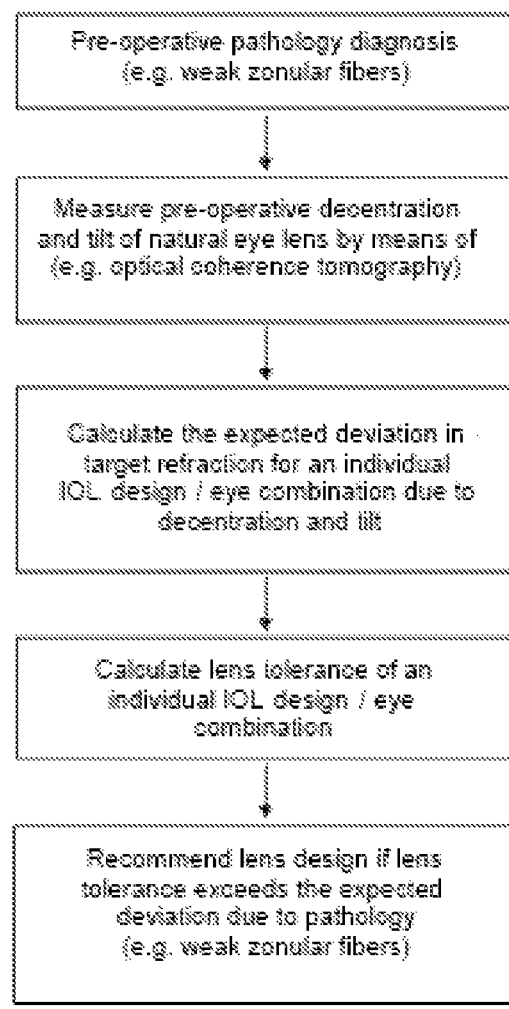
FIG. 3: is a flowchart for the quantitative selection of an IOL as a function of incision-related changes; and, FIG. 4: is a flowchart for the quantitative selection of an IOL as a function of preoperative, diagnosable, pathological indications.

In this regard FIG. 3 provides a flowchart for the quantitative selection of an IOL as a function of preoperatively diagnosable pathological indications.

Proceeding from an established and measured decentration and/or tilt of the natural eye lens, corresponding expected post-operative values that characterize the expected deviations from the target refraction are determined.

In a fifth embodiment of the inventive method, post-operative incision-related changes in the cornea are taken into account as an additional parameter.

This for example occurs in that the expected incision-related changes in the cornea are predicted from statistics for post-operative changes determined for a population and included in the calculation for the eye model.

In contrast to the previously described embodiments of the method, the parameter that is also to be included in the calculation for improving the selection does not relate to any post-operative effects of the selected IOL but rather relates to the surgical technique used.

A quantitative criterion for the selection of a suitable IOL are post-operative incision-related changes in the cornea, regardless of whether these changes in the cornea necessarily resulted or, as for instance with the "limbal relaxing incision," are desired. With this technique, intentionally larger incisions are made in the cornea in order to cause changes, due to the subsequent wound healing, that for instance lead to a reduction in astigmatism.

In this case, as a function of the incision technique, the mean post-operative change in the cornea is taken into account in the IOL refractive power. To this end, as a function of the general or surgeon-specific incision technique, the mean post-operative change in the cornea of a population is determined. This change is then used in the pre-operative calculation of the residual refraction of an individual IOL-eye combination. For this, the mean post-operative change in the cornea for a population is determined in that the differences in the pre-operative and post-operative keratometer values or the parameterized or point difference in the pre-operative and post-operative topography of the cornea are determined.

On the other hand, the standard deviation for the mean post-operative change in the cornea is used to find the correct IOL for an individual IOL-eye combination. The IOL whose characteristic number LT exceeds the incision-related post-operative standard deviation for the change in the cornea is selected.

Figure 4:
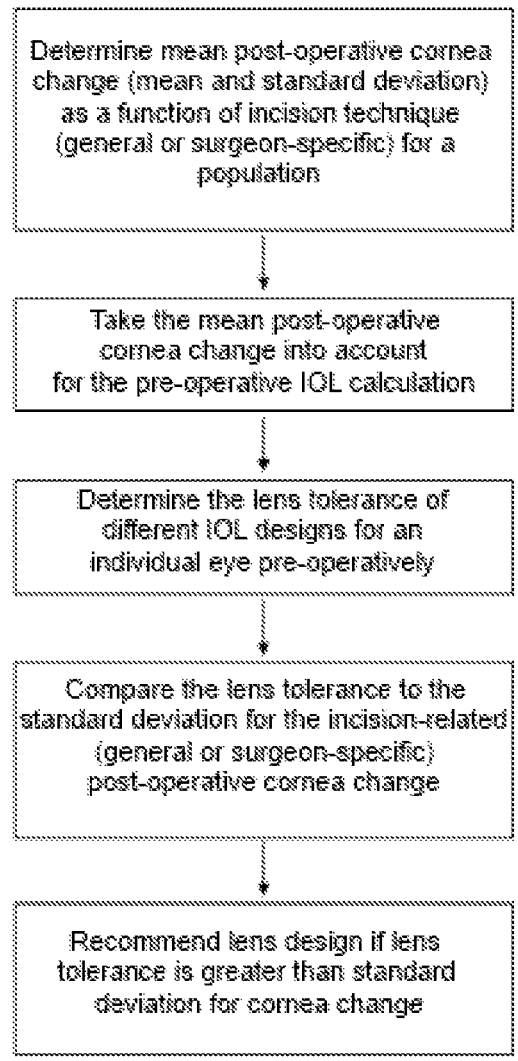

In the regard, FIG. 4 provides a flowchart for the quantitative selection of an IOL as a function of incision-related changes. The mean post-operative change in the cornea is determined for a population in the form of mean and standard deviation as a function of the incision technique and the surgeon and is taken into account in the selection of a suitable IOL.

It is particularly advantageous to take into account the incision-related mean changes in the cornea for the individual eye model so that then at least one of the previously described parameters may also be taken into account. This applies to the post-operatively achievable depth of field, the preferred visual tasks range, and also to incorrect post-operative positioning in the eye.

The mean post-operative change in the cornea is determined for a population in the form of mean and standard deviation as a function of the incision technique and the surgeon and is taken into account in the selection of a suitable IOL.

It is particularly advantageous to take into account the incision-related mean changes in the cornea for the individual eye model so that then at least one of the previously described parameters may also be taken into account. This applies to the post-operatively achievable depth of field, the preferred visual tasks range, and also to incorrect post-operative positioning in the eye.

With the inventive solution, a method for the pre-operative selection of an intraocular lens that is to be implanted in an eye is made available in which the decision for the selection of an IOL is not so highly dependent on the experience of the doctor. On the contrary, it is possible for the doctor to compare potentially suitable IOLs to one another and to take into account special requirements, criteria, and parameters during the selection process. This simplifies the selection process and improves the results of the refractive intervention in the eye.

The invention claimed is:

1. A method for pre-operative selection of an intraocular lens (IOL) to be implanted in an eye, based on an eye model having the individual biometric parameters of the eye, comprising:
   selecting potentially suitable IOLs using optical parameters thereof selected from a group consisting of optical power, asphericity, and toricity, and calculating a residual refraction by application of ray tracing for the potentially suitable IOLs,
   using one of various metrics for calculating the residual refraction and
   for improving the selection, including in the calculation at least one additional parameter that takes into account pre-operative features of the eye, post-operative effects of the selected IOL or surgical technique used.

2. The method in accordance with claim 1, wherein the metrics comprise retinal image metrics.

3. The method in accordance with claim 1, further comprising taking into account post-operatively achievable depth of field as an additional parameter during the selection of the IOL to be implanted in an eye.

4. The method in accordance with claim 1, further comprising taking into account post-operatively achievable depth of field; and
   establishing a limit for a minimum visual acuity and determining from the limit for a minimum visual acuity the usable visual tasks range for the potentially suitable IOLs and using the usable visual tasks range for the potentially suitable IOLs as a selection criterion.

5. The method in accordance with claim 4, wherein the metrics used comprise retinal image metrics for the post-operatively achievable depth of field.

6. The method in accordance with claim 4, wherein the limit for minimum visual acuity is 0.6 or less.

7. The method in accordance with claim 4, wherein the limit for minimum visual acuity is 0.7.

8. The method in accordance with claim 4, wherein the limit for minimum visual acuity is 0.8.

9. The method in accordance with claim 1, further comprising taking into account a visual tasks range preferred by the patient.

10. The method in accordance with claim 9, further comprising taking into account the visual tasks range preferred by the patient such that, with the metrics used, potentially suitable IOLs are determined that correspond to the visual tasks range preferred by the patient and that achieve a sufficiently high post-operative depth of field.

$$LT = \sqrt{\frac{(Dez(\pm X))^2 + (Dez(\pm Y))^2 + (Dez(\pm Z))^2 + (Kip(\pm X))^2 + (Kip(\pm Y))^2 + (Rot(\pm Z))^2}{6}}$$

11. The method in accordance with claim 10, wherein the metrics comprise retinal image metrics.

12. The method in accordance with claim 1, further comprising taking into account the IOL tolerance (LT) with respect to incorrect post-operative positioning in the eye as an additional parameter.

13. The method in accordance with claim 12, wherein the quantified characteristic number LT includes at least incorrect positioning perpendicular to a visual axis in vertical and horizontal directions, incorrect positioning along the visual axis, a tilt in vertical and horizontal directions, or a rotation about the visual axis.

14. The method in accordance with claim 12, wherein the characteristic number LT for the tolerance with respect to incorrect post-operative positioning is quantified using the following formula:

$$LT = \sqrt{\frac{(Dez(\pm X))^2 + (Dez(\pm Y))^2 + (Dez(\pm Z))^2 + (Kip(\pm X))^2 + (Kip(\pm Y))^2 + (Rot(\pm Z))^2}{6}}$$

where LT defines a characteristic number for tolerance
Dez(±X) defines a spherical equivalent (Sph+Cyl/2) of a horizontal deviation from the target refraction
Dez(±Y) defines a spherical equivalent (Sph+Cyl/2) of a vertical deviation from the target refraction
Dez(±Z) defines a spherical deviation from the target refraction due to axial displacement
Kip(±X) defines a spherical equivalent (Sph+Cyl/2)of a deviation from the target refraction due to horizontal tilt
Kip(±Y) defines a spherical equivalent (Sph+Cyl/2) of a deviation from the target refraction due to vertical tilt
Rot(±Z) defines a resultant cylindrical deviation from the target refraction due to axial rotation wherein all values are calculated and/or provided in diopters, in units of retinal image metrics, or in relative units.

15. The method in accordance with claim 12, further comprising taking into account a clinically likely incorrect positioning such that the characteristic figure LT is determined using a defined incorrect positioning or with a given characteristic number LT the degree of the "allowable" incorrect positioning is determined for potentially suitable IOLs.

16. The method in accordance with claim 1, further comprising taking into account the lens tolerance with respect to incorrect post-operative positioning of the IOL such that a characteristic number LT is quantified for a clinically likely incorrect positioning.

17. The method in accordance with claim 16, wherein the quantified characteristic number LT includes at least incorrect positioning perpendicular to a visual axis in vertical and horizontal directions, incorrect positioning along the visual axis, a tilt in the vertical and horizontal directions, or a rotation about the visual axis.

18. The method in accordance with claim 16, wherein the characteristic number LT for the tolerance with respect to incorrect post-operative positioning is quantified using the following formula:

where LT defines a characteristic number for tolerance
Dez(±X) defines a spherical equivalent (Sph+Cyl/2) of a horizontal deviation from the target refraction
Dez(±Y) defines a spherical equivalent (Sph+Cyl/2) of a vertical deviation from the target refraction
Dez(±Z) defines a spherical deviation from the target refraction due to axial displacement
Kip(±X) defines a spherical equivalent (Sph+Cyl/2) of a deviation from the target refraction due to horizontal tilt
Kip(±Y) defines a spherical equivalent (Sph+Cyl/2) of a deviation from the target refraction due to vertical tilt
Rot(±Z) defines a resultant cylindrical deviation from the target refraction due to axial rotation wherein all values are calculated and/or provided in diopters, in units of retinal image metrics, or in relative units.

19. The method in accordance with claim 16, further comprising taking into account a clinically likely incorrect positioning such that the characteristic figure LT is determined using a defined incorrect positioning or with a given characteristic number LT the degree of the "allowable" incorrect positioning is determined for potentially suitable IOLs.

20. The method in accordance with claim 1, further comprising, for improving the selection, including an additional parameter that takes into account the pre-operative features of the eye in the calculation.

21. The method in accordance with claim 20, wherein the preoperative features include pre-operatively diagnosable pathological indications.

22. The method in accordance with claim 20, further comprising taking into account expected post-operative fluctuations in the target refraction.

23. The method in accordance with claim 22, further comprising measuring values for decentration and tilt of the natural eye lens relative to the center of the pupil and/or limbus and determining expected post-operative values therefrom.

24. The method in accordance with claim 1, further comprising taking into account pre-operatively diagnosable pathological indications such that they are measured and taken into account as expected post-operative fluctuations in the target refraction.

25. The method in accordance with claim 24, further comprising taking into account expected post-operative fluctuations in the target refraction.

26. The method in accordance with claim 25, further comprising measuring values for decentration and tilt of the natural eye lens relative to the center of the pupil and/or limbus and determining expected post-operative values therefrom.

27. The method in accordance with claim 1, further comprising taking into account post-operative incision-related changes in the cornea as an additional parameter.

28. The method in accordance with 27, wherein post-operative incision-related changes in the cornea are taken into account in that the expected incision-related changes in the cornea are predicted from statistics for post-operative changes determined for a population and included in the calculation for the eye model.

29. The method in accordance with claim 28, further comprising determining a mean post-operative change in the cornea for a population by determining differences in pre-operative and post-operative keratometer values or parameterized or point differences in the pre-operative and post-operative topography of the cornea.

30. The method in accordance with claim 27, further comprising determining a mean post-operative change in the cornea for a population by determining differences in pre-operative and post-operative keratometer values or parameterized or point differences in the pre-operative and post-operative topography of the cornea.

* * * * *